United States Patent [19]

Blount

[11] 4,036,787

[45] July 19, 1977

[54] PROCESS FOR THE PRODUCTION OF EPOXY SILICATE COMPOUNDS AND POLYMERS

[76] Inventor: David H. Blount, 5450 Lea St., San Diego, Calif. 92105

[21] Appl. No.: 678,196

[22] Filed: Apr. 19, 1976

Related U.S. Application Data

[63] Continuation-in-part of Ser. No. 612,844, Sept. 12, 1975, abandoned, which is a continuation-in-part of Ser. No. 262,485, June 14, 1972, abandoned.

[51] Int. Cl.[2] ............................................... C08G 77/02

[52] U.S. Cl. ................................ 260/2 S; 106/287 S; 260/2 EP; 260/2 EC; 260/47 EP; 260/2 BP; 260/47 EC; 260/78 S; 260/78 SC; 260/404; 423/324; 423/325; 423/326

[58] Field of Search ..................... 106/287 S; 260/2 S, 260/2 EP, 2 EC, 2 BP, 47 EP, 47 EC, 78 S, 78 SC, 404; 423/324, 325, 326

[56] References Cited

U.S. PATENT DOCUMENTS 3,956,466 5/1976 Blount .................................. 423/325

OTHER PUBLICATIONS

Noller, Chemistry of Organic Compounds, W. B. Saunders, Philadelphia, 1965, p. 813.

*Primary Examiner*—Melvyn I. Marquis

[57] ABSTRACT

Silicic acid and epoxy compounds are reacted to produce epoxy silicate compounds, and polymers, when mixed together in the presence of a suitable catalyst.

10 Claims, No Drawings

PROCESS FOR THE PRODUCTION OF EPOXY SILICATE COMPOUNDS AND POLYMERS

CROSS-REFERENCE TO RELATED APPLICATIONS

This application is a continuation-in-part of my copending U.S. Patent Application Ser. No. 612,844; filed Sept. 12, 1975, now abandoned, which is a continuation-in-part of my earlier U.S. Patent Application No. 262,485, filed June 14, 1972, now abandoned.

BACKGROUND OF THE INVENTION

This invention relates to the production of epoxy silicate compounds and polymers, and will be referred to as epoxy silicate polymers for the purposes of this application.

Various silicic acids may be used in this process such as, air dried silicic acid gel, and, metasilicic acid. The metasilicic acid and silicic acid gel may be produced by any of the well known methods, such as adding an acid to an aqueous solution of sodium metasilicate and precipitating the silicic acid gel.

While a wide variety of epoxy compounds have been produced for a number of diverse applications, none have the unique properties possessed by the compounds of this invention. Epoxy silicate polymers may be used as molding materials, as coating agents, in dispersions, adhesives, as fillers, in casting applications, as prepolymers, as impregnates, in rubber-like materials and may be copolymerized with other organic reactants. They may also be used as intermediates in the production of further compounds.

SUMMARY OF THE INVENTION

I have discovered that silicic acid, when mixed in appropriate proportions with a suitable epoxy compound and a suitable catalyst, will react chemically to produce an epoxy silicate polymer. This basic process may be varied to produce products having varied properties. The proportions of silicic acid, catalyst and epoxy compound may be varied, for example, to produce a polymer ranging from very hard to soft and rubbery.

The reactants may be mixed in any suitable proportions, depending upon the product characteristics desired. Generally, from about 0.1 to about 3 mols of the epoxy compound are mixed with each mol of silicic acid (the mols of silicic acid are calculated on the basis of its silicon dioxide content). A catalytically effective amount of the selected catalyst is used. Generally, depending upon the catalyst selected and the reaction conditions desired, where the catalyst, such as some amines, also enters into the reaction, a larger quantity may be desirable. In most cases, from about 0.02 to 2 parts catalyst per part silicic acid will give good results.

In one preferred embodiment of this invention, a thermoplastic polymer having excellent properties is produced by mixing the silicic acid and a suitable amine catalyst, then adding the epoxy compound in steps of about 10 to 20 percent of the total, allowing the reaction to be completed for each step before additional epoxy compound is added. Generally, with agitation, only a few minutes need be allowed between addition of steps.

Any suitable epoxy compound may be used in this process. Typical epoxy compounds include epichlorohydrin, glycidol, methyl epichlorohydrin, 1,2-epoxy-3-phenoxypropane, 3,4-epoxyethyl benzene, 1,8-epoxy-p-menthane, 1,2-epoxybutane, 1,2-epoxycyclokexane, epoxyethane, 1,2-epoxypropane, 1-chloro-2,3-epoxypropane, 1:2,3:4-diepoxybutane, 2:3,6:7-diepoxy-2,6-dimethyl-4-octene, epoxyethylbenzene and mixtures thereof. Of these, best results are obtained with epichlorohydrin which is therefore, the preferred epoxy compound.

In an alternative embodiment, the epoxy compound, such as epichlorohydrin may be initially at least partially reacted with a suitable dihydroxy organic compound such as Bisphenol-A, resorcinol, hydroquinone glycol, glycerol or a di-(mono-hydroxy) alkane to produce an intermediate or prepolymer which is then reacted with silicic acid to produce epoxy silicate polymers.

Any suitable catalyst may be used to initiate, promote or modify the chemical reaction. Typical catalysts include various mineral acids, Lewis acids and organic compounds. Organic amines have been found to both act as a catalyst and enter into the reaction and become part of the epoxy silicic acid product. The amine may be primarily reacted with the silicic acid to form silicic amides which are then reacted with the epoxy compounds. Aliphatic and aromatic amines have been found to be most useful. Primary amines are more effective than secondary and tertiary amines and are, therefore, preferred. Optimum results have been obtained with polyfunctional aliphatic amines such as diethylene triamine, since the reaction takes place rapidly at room temperature to form apparently highly cross-linked structures. If desired, complex or adduct amines may be used. Typical amines include methylamine, ethylamine, propylamine, isopropylamine, butylamine, amylamine, hexylamine, aniline, toluidine amine, xylidene amine, phenylenediamine, naphthylamine, benzylamine, ethylenediamine, tetramethylenediamine, pentamethylenediamine, hexamethylenediamine, octamethylenediamine, decamethylenediamine, xylylenediamine, piperazine and other compounds which end with an amine radical, such as aminocaproic acid, alkylene polyamines, alkamines, vinyl amines, diethylenetriamine, triethylenetetramine, tetraethylenepentamine, tetramethylenediamine and mixtures thereof.

Any suitable modifying or additive compounds may be used in the reaction of this invention to vary the properties of the product. Typical additives include dicarboxylic anhydrides, polysulfides polymers, silico-aminoplasts, silicate aminoplasts, silico-phenoplasts, silicate phenoplasts, aminoplasts, phenoplasts, fatty or resin acids, silico-furan polymers, silicate furan polymers, furfural-ketone resins, dibutyl phthalate, tricresyl phosphate, cresyl silicates, polyamides, fatty diamines, styrene oxide, acetonitrile, primary aromatic sulfonamides, secondary aromatic sulfonamides, disecondary sulfonamides, polymerized oils, carbon disulfide, soya bean oil, polyamide resins and mixtures thereof.

The reactions of this invention may take place under any suitable physical condition. While many of the reactions will take place acceptable at ambient temperature and pressures, in some cases, better results may be obtained at somewhat elevated temperatures and pressures. Preferably, the reaction takes place at a temperature between 50° C and the boiling point of the solution. On the other hand, where the reaction is exothermic, it may be desirable to cool the reaction vessel. With some products it is desirable to raise the pH after the reaction is complete to at least about 7 to precipitate the polymer.

While all of the details of the reactions which take place are not fully understood, it appears that the silicic acid generally reacts with the epoxy radical of the epoxy compound. The reaction is theorized to take place as follows: Epichlorohydrin is theorized to react with metasilicic acid as follows:

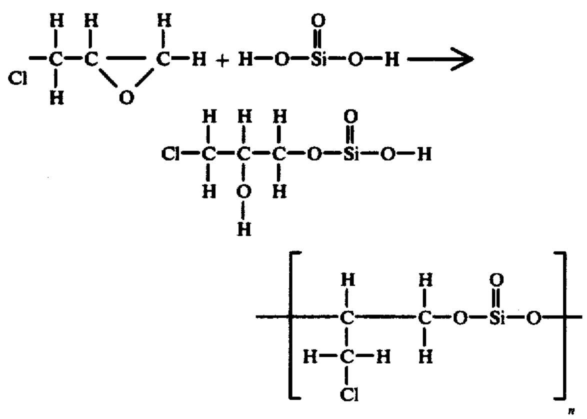

Epichlororohydrin and a diamine is theorized to react with metasilicic acid as follows:

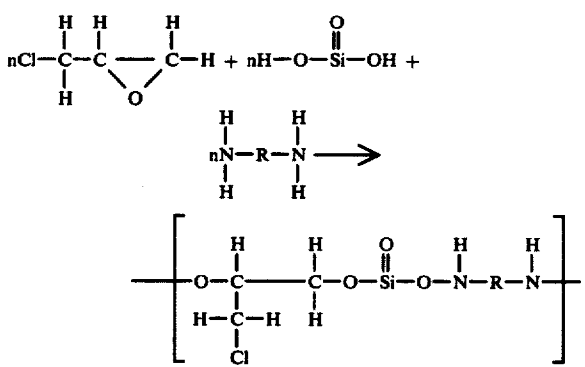

Where R is selected from the group consisting of alkyl, alkylene, alka alkylene polyamino and benzyl radicals. Where *n* is a positive integer greater than 1.

DESCRIPTION OF PREFERRED EMBODIMENTS

My invention will be illustrated in greater detail in the specific examples which follow, which detail preferred embodiments of my process. It should be understood that the scope of my invention is not limited to the specific processes set out in the examples. Parts and percentages are by weight, unless otherwise indicated.

EXAMPLE I

About 20 parts by weight of silicic acid gel air dried at 25° to 50° C, 20 parts by weight of epichlorohydrin and 2 parts by weight of phosphorous acid are mixed at ambient temperature and pressure for 10 to 25 minutes, thereby producing a tan, granular, solid mixture of epichlorohydrin silicate and poly(epichlorohydrin silicate) polymer.

The said tan granular solid is soluble in acetic acid, alcohol, epichlorohydrin and other organic solvents. The said tan granules were added to acetic acid, and a solution was produced then filtered. About 15 to 25% of the silicic acid was filtered out of the solution and appeared to be unreacted. The solution of epichlorohydrin silicate may be painted on wood and forms a protective coating.

EXAMPLE II 40 parts by weight of dry sodium metasilicate is mixed with 200 parts by weight of water. The sodium metasilicate goes into solution and then dilute sulfuric acid is added slowly until the pH is about 7 and silicic acid gel is produced. The silicic acid gel is washed and filtered, then compressed to remove the excess water and air dried at 25° to 50° C. The dry silicic acid gel is pulverized into a powder.

About 20 parts by weight of silicic acid gel powder are mixed with 20 parts by weight of epichlorohydrin, then about 3 parts by weight of 6 normal sulfuric acid are added while agitating; the reaction is complete in 10 to 30 minutes at ambient temperature and pressure, thereby producing light tan granules of epichlorohydrin silicate and poly(epichlorohydrin silicate) polymer. The said granules are soluble in water, dilute sulfuric acid, alcohol, acetic acid and other organic solvents.

EXAMPLE III 40 parts by weight of dry granular sodium metasilicate are dissolved in 200 parts by weight of water, then dilute sulfuric acid is added until the pH is about 7 and the solution gels, thereby producing silicic acid gel which is washed with water and filtered; excess water is then pressed out of the silicic acid gel.

The said moist silicic acid gel is added to 25 parts by weight of diethylene triamine then heated to just below the boiling point of diethylene triamine while agitating for about 20 to 60 minutes, thereby producing a yellow powder, diethylene triamine silicate and poly(diethylene triamine silicate) polymer. 25 parts by weight of epichlorohydrin is added to said yellow powder then agitated for 10 to 30 minutes thereby producing a light yellow colored resin.

EXAMPLE IV

Moist silicic acid gel equivalent to 25 parts by weight of dry silicic acid gel are mixed with 30 parts by weight of ethylene diamine, then heated to just below the boiling point of ethylene diamine for 15 to 25 minutes, thereby producing a yellow powder, ethylene diamine silicate and poly(ethylene diamine silicate) polymer.

25 parts by weight of epichlorohydrin are mixed with the said yellow powder then agitated for 10 to 20 minutes, thereby producing a polymer.

EXAMPLE V

About 40 parts by weight dry powdered metasilicic acid, about 5 parts by weight of ethylamine, and about 50 parts by weight of epichlorohydrin are mixed, then heated to about the boiling point of epichlorohydrin while agitating for about 30 minutes, thereby producing poly(epichlorohydrin silicate) polymer.

EXAMPLE VI 20 parts by weight of silicoformic acid, 25 parts by weight of triethylenetetramine, 10 parts by weight of sodium metasilicate pentahydrate and 25 parts by weight of epichlorohydrin are mixed and agitated for about 15 to 30 minutes, thereby producing a light yellow rubbery poly(triethylenetetramine epichlorohydrin silicoformate) polymer.

EXAMPLE VII

About 10 parts by weight of air dried silicic acid gel, 5 parts by weight of Bisphenol A epoxy polymer, 5 parts by weight of epichlorohydrin and 10 parts by weight of diethylene triamine are mixed then heated to about 40° C for 5 to 20 minutes thereby producing a soft yellow epoxy silicate polymer.

EXAMPLE VIII

About 20 parts by weight of air dried metasilicic acid powder about 20 parts by weight of caprolactam and about 25 parts by weight of epichlorohydrin are mixed then heated to about the boiling point of epichlorohydrin while agitating for about 10 to 20 minutes, then heated to about 150° C for about 20 minutes, thereby producing polymer, a solid polymer which will melt and may be molded into useful objects.

EXAMPLE IX

About 30 parts by weight of metasilicic acid powder, 20 parts by weight of p-aminobenzoic acid and 35 parts by weight of epichlorohydrin are mixed, then heated to just below the boiling point of epichlorohydrin while agitating at ambient pressure for 20 to 40 minutes and then gradually elevating the temperature to about 120° C for 20 to 40 minutes, thereby producing a tan hard polymer. The said polymer may be melted and molded into useful objects.

EXAMPLE X

About 20 parts by weight of room air dried silicic acid gel powder, 10 parts by weight of polyamide resin(-linoleic acid and diethylene triamine polymerized) and about 30 parts by weight of epichlorohydrin are mixed, then heated to about 50° to 65° C while agitating for about 25 to 40 minutes, thereby producing a light yellow polymer.

EXAMPLE XI

About 10 parts by weight of room air dried silicic acid gel powder, 10 parts by weight of diethylene triamine and 10 parts by weight of 1,2-epoxypropane are mixed and agitated for 10 to 30 minutes at ambient temperature and pressure, thereby producing a light yellow polymer.

EXAMPLE XII

Moist silicic acid gel equivalent to about 25 parts by weight of dry silicic acid gel and 25 parts by weight of 1,6-hexanediamine are mixed and heated to 70° to 95° C while agitating for 20 to 40 minutes, thereby producing a white granular compound, hexanediamine silicate.

25 parts by weight of epichlorohydrin are added to the said hexanediamine silicate then heated to about 45° to 55° C while agitating for about 20 to 40 minutes, thereby producing a light brown liquid polymer. The said polymer is thermoplastic and when heated to about 80° C it becomes a light brown rubbery polymer. The liquid polymer may be poured into molds then heated to about 80° C, thereby forming useful solid objects.

EXAMPLE XIII 20 parts by weight of room air dried silicic acid gel powder, 5 parts by weight of diethylene triamine and 10 parts by weight of 3-chloropropene are mixed, then 25 parts by weight of epichlorohydrin are added on parts of 5 parts by weight and mixed then heated to 40° to 50° C while agitating at ambient pressure for 10 to 15 minutes; then another 5 parts by weight are added and treated the same way. This is repeated until the 25 parts by weight are added, thereby producing a thick liquid polymer. The thick cream colored liquid is cured by heating to about 80° C into a tough hard rubbery resin.

EXAMPLE XIV 20 parts by weight of silicic acid gel, air dried at 25° to 60° C, 20 parts by weight of phenol and 2 parts by weight of sodium carbonate are mixed then heated to just below the boiling point of the phenol for 20 to 40 minutes while agitating, thereby producing a mixture of phenol silicate and silicic acid gel. 20 parts by weight of epichlorohydrin are added and mixed with said mixture then heated to just below the boiling point of epichlorohydrin for 15 to 30 minutes while agitating, thereby producing a mixture of epoxy phenol silicate, silicic acid gel and epichlorohydrin. About 10 parts by weight of diethylene triamine are added to said mixture and agitated for 10 to 25 minutes, thereby producing an orange colored rubbery resin.

EXAMPLE XV 20 parts by weight of dry silicic acid gel, 20 parts by weight of maleic anhydride and 3 parts by weight of sodium carbonate are mixed, then heated to above the melting point of maleic anhydride for 20 to 30 minutes while agitating, thereby producing tan granules of maleic silicate and silicic acid gel. 30 parts by weight of epichlorohydrin are added to said maleic silicate and silicic acid gel, then the mixture is heated to 40° to 50° C for 20 to 30 minutes while agitating, thereby producing a thick, tan liquid, poly(epoxy maleic silicate) polymer and silicic acid gel. The said liquid polymer is cured by adding 10 parts by weight of diethylene triamine then mixing for 10 to 20 minutes, thereby producing an orange colored solid tough resin. The said resin softens at about 80° C and melts at about 110° C and may be molded into useful objects. The said resin is soluble in acetic acid; the solution may be painted on wood and forms a tough protective coating.

Although specific conditions and ingredients have been described in conjunction with the above examples of preferred embodiments, these may be varied and other reagents and additives may be used, where suitable, as described above, with similar results.

Other modifications and applications of this invention will occur to those skilled in the art upon reading this disclosure. These are intended to be included within the scope of this invention, as defined in the appended claims.

I claim:

1. The process for the production of epoxy silicate polymers by the following steps:

a. adding about 10 parts by weight of a silicic acid gel;
b. mixing therewith 5 to 20 parts by weight of an organic epoxy compound havng at least one epoxy group;
c. mixing therewith a catalytic amount of organic amine compounds; and
d. agitating the mixture until the resulting chemical reaction is complete.

2. The process according to claim 1 wherein said organic epoxy compound is selected from the group consisting of epichlorohydrin, 1,2-epoxy-3-phenoxypropane, 3,4-epoxyethyl benzene, 1,2-epoxybutane, 1,2-epoxycyclohexane, epoxyethane, 1,2-epoxypropane, 1-chloro-2,3 epoxypropane, 1:2,3:4-diepoxybutane, epoxyethylbenzene and mixtures thereof.

3. The process according to claim 1 wherein said organic epoxy compound comprises epichlorohydrin.

4. The process according to claim 1 wherein said catalyst is added to said silicic acid prior to the addition of said organic epoxy compound thereto, and said epoxy compound is added in steps of about 10 to 20 weight percent of the total epoxy compound, while allowing the reaction following each addition to reach substantial completion before addition of the next step.

5. The process according to claim 1 wherein said catalyst is an organic amine selected from the group consisting of primary aliphatic and aromatic amines.

6. The process according to claim 5 including the further step of adding an alkali compound selected from the group consisting of sodium hydroxide, sodium hydroxide, potassium hydroxide and potassium carbonate with the said organic amine in the proportion of one mol to each 2 mols of the halide present in the epoxy compound.

7. The process according to claim 1 wherein said mixture is maintained at a temperature of between about 50° C and the boiling temperature of said mixture during the reaction period.

8. The process according to claim 1 wherein said silicic acid is first reacted with the amine catalyst consisting of a polyamine selected from the group consisting of phenylenediamine, ethylenediamine, tetramethylenediamine, pentamethylenediamine, hexamethylenediamine, octamethylenediamine, decamethylenediamine, xylylenediamine, piperazine, alkylene polyamines, diethylenetriamine, triethylenetriamine, tetraethylenepentamine, tetramethylenediamine and mixtures thereof, by mixing the said silicic acid with the amine compound then heating the mixture to just below the boiling point of the amine compound for 20 to 40 minutes, thereby producing an aminosilicate compound.

9. The process according to claim 1 wherein 10 parts by weight of silicic acid are mixed with 5 to 10 parts by weight of an organic amine selected from the group consisting of primary aliphatic amines and aromatic amines; then 5 to 10 parts by weight of epichlorohydrin are added in proportion of 1 to 2 parts by weight while agitating until the chemical reaction is substantially complete.

10. The process according to claim 1 wherein the silicic acid is metasilicic acid.

* * * * *